(12) United States Patent
Sillers (10) Patent No.: US 11,034,982 B2
(45) Date of Patent: Jun. 15, 2021

(54) GENETICALLY MODIFIED YEAST WITH INCREASED SUCCINIC ACID PRODUCTION

(71) Applicant: PTT GLOBAL CHEMICAL PUBLIC COMPANY LIMITED, Bangkok (TH)

(72) Inventor: Ryan Sillers, Reading, MA (US)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 0 days.

(21) Appl. No.: 16/626,676

(22) PCT Filed: May 23, 2018

(86) PCT No.: PCT/US2018/034121
§ 371 (c)(1),
(2) Date: Dec. 26, 2019

(87) PCT Pub. No.: WO2019/005340
PCT Pub. Date: Jan. 3, 2019

(65) Prior Publication Data
US 2020/0157583 A1 May 21, 2020

Related U.S. Application Data

(60) Provisional application No. 62/527,351, filed on Jun. 30, 2017.

(51) Int. Cl.
*C12N 15/81* (2006.01)
*C12P 7/46* (2006.01)

(52) U.S. Cl.
CPC ..................... *C12P 7/46* (2013.01)

(58) Field of Classification Search
CPC ....... C12N 15/81; C12N 15/52; C12P 9/0004; C12P 7/46
See application file for complete search history.

(56) References Cited

U.S. PATENT DOCUMENTS

| 2007/0042476 A1 | 2/2007 | Lee et al. |
| 2007/0042481 A1 | 2/2007 | Lee et al. |
| 2008/0020436 A1 | 1/2008 | Lee et al. |
| 2014/0363862 A1 | 12/2014 | Rush et al. |
| 2015/0176038 A1 | 6/2015 | Rush et al. |
| 2015/0240270 A1* | 8/2015 | Yocum ............... C12N 15/52 435/139 |

FOREIGN PATENT DOCUMENTS

| WO | WO 2013/112939 A2 | 1/2013 |
| WO | WO 2014/018755 A1 | 1/2014 |

OTHER PUBLICATIONS

International Search Report dated Oct. 10, 2018 in PCT/US2018/034121, 8 pages.
Xiao, H., et al., "Exploiting *Issatchenkia orientalis* SD108 for succinic acid production", Microbial Cell Factories, vol. 13, 2014, XP021196416, pp. 1-11.
Yan, D., et al., "Construction of reductive pathway in *Saccharomyces cerevisiae* for effective succinic acid fermentation at low pH value", Bioresource Technology, vol. 156, 2014, XP055279282, pp. 232-239.
Cao, Y., et al., "Fermentative Succinate Production: An Emerging Technology to Replace the Traditional Petrochemical Processes", BioMed Research International, vol. 95, No. 4, 2013, XP055093617, 12 pages with cover page.
Balzer, G.J., et al., "Metabolic engineering of *Escherichia coli* to minimize byproduct formate and improving succinate productivity through increasing NADH availability by heterologous expression of $NAD^+$-dependent formate dehydrogenase", Metabolic Engineering, vol. 20, 2013, XP055491098, pp. 1-8.
Ahn, J.H., et al., "Production of succinic acid by metabolically engineered microorganisms", Current Opinion in Biotechnology, vol. 42, 2016, XP029831135, pp. 54-66.
Raab, A.M., et al., "Oxidative versus reductive succinic acid production in the yeast *Saccharomyces cerevisiae*", Bioengineered Bugs, vol. 2 No. 2, Mar. 2011, pp. 120-123 with cover page.
Zelle, R.M., et al., "Anaplerotic Role for Cytosolic Malic Enzyme in Engineered *Saccharomyces cerevisiae* Strains", Applied and Environmental Microbiology, Feb. 2011, vol. 77 No. 3, XP055054162, pp. 732-738.
De Kok, S., et al., "Energy coupling in *Saccharomyces cerevisiae*: selected opportunities for metabolic engineering", FEMS Yeast Research, vol. 12, 2012, XP055087573, pp. 387-397.
Stols, L., et al., "Production of Succinic Acid through Overexpression of $NAD^+$-Dependent Malic Enzyme in an *Escherichia coli* Mutant", Applied and Environmental Microbiology, vol. 63 No. 7, Jul. 1997, XP003003683, pp. 2695-2701.
Hong, S.H., et al., "Enhanced Production of Succinic Acid by Metabolically Engineered *Escherichia coli* with Amplified Activities of Malic Enzyme and Fumarase", Biotechnology and Bioprocess Engineering, vol. 9 No. 4, 2004, XP002395349, pp. 252-255.

* cited by examiner

*Primary Examiner* — Tekchand Saidha
(74) *Attorney, Agent, or Firm* — Oblon, McClelland, Maier & Neustadt, L.L.P.

(57) ABSTRACT

Improved yeast cell with increased succinic acid production based on yield and titer. Increased activity of one or more enzymes involved in the pentose phosphate pathway, reducing flux through phosphoglucose isomerase, increasing flux to cytoplasmic acetyl-CoA, installation of a malic enzyme, and/or installation of a formate dehydrogenase leads to increased production of succinic acid.

6 Claims, 7 Drawing Sheets

GENETICALLY MODIFIED YEAST WITH INCREASED SUCCINIC ACID PRODUCTION

CROSS-REFERENCE TO RELATED APPLICATIONS

This application claims priority to U.S. Provisional Patent Application No. 62/527,351 filed Jun. 30, 2017.

STATEMENT REGARDING FEDERALLY SPONSORED RESEARCH OR DEVELOPMENT

Not Applicable.

JOINT RESEARCH AGREEMENT

Not applicable.

BACKGROUND OF INVENTION

The invention relates to the field of bio-based chemical production. More specifically, the invention relates to producing succinic acid from renewable carbon sources using genetically modified yeast.

Succinic acid is an intermediate in the tricarboxylic acid (TCA) cycle and many bacteria are known to have the natural ability to produce succinate as a major fermentation product. The commercial demand for succinic acid or a salt of succinic acid (both also referred to as "succinate") is expanding. A 2004 U.S. Department of Energy report entitled, "Top Value Added Chemicals from Biomass" identified succinic acid as one of twelve building block chemicals that can be produced from renewable feedstock. Succinic acid is used as a starting material in the manufacture of number of specialty chemicals such as 1, 4-butanediol, tetrahydrofuran, gamma-butryolactone and N-methylpyrrolidone. Succinic acid as a large volume chemical has the potential to be used in the manufacture of various products, including animal feed, plasticizers, congealers, polymers, fibers, and plastics, most notably polybutyl succinate (also referred to as "polybutylene succinate" or "PBS"). Many of the polymers made from succinate biodegrade at a much faster rate than other polymers derived from petroleum such as polyethylene, polypropylene, polystyrene, and polyethylene terephthalate (PET). As such, plastics made from succinate are highly desirable, since they will decay more quickly in landfills or other composting environments (Kunioka, Ninomiya, & Funabashi, 2009). This property extends to many other polymers and plastics where the monomeric subunits are biologically derived compounds or their chemical equivalent, rather than petrochemically derived compounds that are not normally found abundantly in living organisms. For example, polymers derived from fumaric acid (fumarate), malic acid (malate), adipic acid (adipate), L-lactic acid (L-lactate), D-lactic acid (D-lactate), and/or other naturally occurring organic acids, are all degraded more readily than many petrochemically derived polymers in composting environments. As such, for the benefit of humanity, it is desirable to replace polymers and plastics currently made from petrochemicals with polymers and plastics made from biochemicals.

Many biochemicals, such as succinate, fumarate, and adipate, can be manufactured from petroleum, and many currently used processes for making PBS and nylons use petroleum-derived monomers. However, since the world's petroleum supply is finite, it would also be desirable to develop materials and methods for producing biochemical monomers by fermentation from renewable carbon sources such as sugars, sugar polymers, glycerol, fatty acids, carbon dioxide, lignin, or any other form of biomass or waste derived from biomass. Thus, it is desirable to develop processes for manufacturing biodegradable plastics from biorenewable resources.

Bioprocesses that produce many of the above mentioned biochemicals use organisms that cannot grow at low pH. Therefore, while the organic acid is being produced, the culture medium must be kept at a pH from about 5 to about 7.5 by addition of base, usually a hydroxide, carbonate, bicarbonate, or a mixture thereof, of sodium, potassium, ammonium, magnesium, or calcium. As a result, the organic acid in the culture broth exists as a salt, and the majority of the organic acid molecules are charged. The charged state presents an advantage and a disadvantage. The advantage is that the charged salt does not easily diffuse back across the cell membrane into the cell. The disadvantage is that the polymerization chemistry or other further chemical use of the organic acid usually requires the protonated form (also referred to as "free acid") of the organic acid, so that the salts produced by fermentation require potentially costly downstream processing to provide the free acid form. As such, it would be advantageous to produce organic acids at low pH (a pH near or, more preferably, below that of the lowest pKa of the organic acid), such that a majority of the molecules are in the free acid state. Other considerations aside, a low pH fermentation broth should be less expensive to process to give a pure preparation of the free acid because much less counter-ion (such as sodium, potassium, ammonium, magnesium, calcium) would have to be supplied during fermentation and then separated to give protonated succinic acid after fermentation.

Several processes exist for the production of organic acids at low pH utilizing various yeasts as production hosts. WO 2012/103261 discloses strains of *Issatchenkia orientalis* that have been engineered to produce succinate or malate. These strains were derived from a wild type parent that was chosen as being the most resistant to high concentrations of succinate at low pH among a collection of many different yeast species. In particular, the *I. orientalis* strain chosen was more resistant to succinate when compared to a *Kluyveromyces marxianus* strain. However, as previously disclosed (WO 2014/043591), a new wild type strain of *K. marxianus* has been isolated that is more tolerant to succinate at low pH than an *I. orientalis* strain, when grown in a rich medium. Thus, there is clearly some variability among different strains within a species with respect to tolerance to organic acids at low pH, and the precise conditions under which the screening is done might influence the outcome of such screens. In addition, *Saccharomyces cerevisiae* strains have been developed for succinate production, but again, the *K. marxianus* strain disclosed (WO 2014/043591) is more resistant to succinate at low pH. Moreover, *K. marxianus* can ferment xylose natively, so it has a second advantage over *S. cerevisiae* as a host yeast for succinate production.

Despite the theoretical advantage of producing dicarboxylic acids, such as succinic acid, in low pH fermentations with yeasts, due to subcellular compartmentalization in the form of membrane-bound organelles in yeasts, engineering succinate production in yeast is not nearly as straight forward as in *E. coli* or other bacteria. First, in *Saccharomyces*, and probably in most, if not all, other yeasts, under aerobic conditions, the TCA cycle operates inside the mitochondria or promitochondria (WO 2008/128522, WO 2010/043197). In the absence of specific succinate transporters, the mitochondrial inner membrane is impermeable to succinate (Lee et al., 2011), but protein transporters are known that import succinate into the mitochondria in exchange for fumarate or phosphate (Palmieri et al., 2000). However, there are no known mechanisms for secreting succinate from the mitochondria to the cytoplasm, so that succinate produced from the TCA cycle, even in a branched mode, would not be easily transported outside of the mitochondria and hence outside of the cell. As such, it was recognized in the prior art that it would be desirable to engineer biosynthesis of dicarboxylic acids such as malate and succinate in the cytoplasm, by arranging for key enzymes in the reductive pathway to malate and succinate, such as pyruvate carboxylase, malate dehydrogenase, and fumarase, to be present and sufficiently active in the cytoplasm, outside of the mitochondria (US 2008/0090273, US 2012/0040422, WO 2010/003728, WO 2011/023700. WO 2009/101180, and WO 2012/038390, WO 2008/128522, WO 2010/043197). However, the prior art has not fully recognized or addressed the problem of how to export succinate from the mitochondria or how to attain redox balance under anaerobic or microaerobic conditions, while maximizing succinate yield from glucose or other carbon source in yeast. Moreover, the regulation of the production and activities of all of the relevant enzymes, both inside and outside the mitochondria, is extremely complicated, and it is not obvious how to engineer appropriate levels. Finally, the mitochondrial membrane is not permeable to NAD and NADH, and it is not obvious how to attain efficient redox balance between the mitochondrial matrix and the cytoplasm under anaerobic or microaerobic conditions. The invention disclosed herein recognizes these challenges and provides solutions to these problems.

SUMMARY OF INVENTION

The present invention provides yeast cells with altered metabolic pathways useful in the production of organic acid such as malic acid, fumaric acid and succinic acid in the cytoplasm. More specifically, the present invention provides yeast cells with redox balanced metabolic pathways operational in the cytoplasm and are useful in the production of succinic acid.

In one embodiment, the recombinant yeast cells of the present invention possess a reductive succinic acid pathway from phosphoenolpyruvate to succinic acid that is operational in the cytoplasm and involves the enzymes pyruvate kinase, malic enzyme, fumarase and fumarate reductase.

In another embodiment, the recombinant yeast cells of the present invention possess a reductive succinic acid pathway from phosphoenolpyruvate to succinic acid and operational within the cytoplasm and involves the enzymes phosphoenolpyruvate carboxylase, phosphoenolpyruvate carboxykinase, malate dehydrogenase, fumarase and fumarate reductase.

The present invention also provides yeast cells wherein the reductive pathway for succinic acid production operational in the cytoplasm is redox-balanced by means of enhancing the operation of a pentose phosphate pathway within the cytoplasm. An increase in the level of reducing equivalents resulting from the enhanced operation of a pentose phosphate pathway helps in satisfying the reducing equivalents required for the operation of a reductive pathway for succinic acid production in the cytoplasm. In one aspect of this embodiment, the enhancement of the operation of pentose phosphate pathway is achieved by means of increasing the activity of a glucose-6-phosphate dehydrogenase enzyme. In another aspect of this embodiment, the enhancement of the operation of pentose phosphate pathway is achieved by means of blocking the activity of phosphoglucose isomerase. In yet another embodiment of the present invention, the enhancement of the operation of a pentose phosphate pathway is achieved by means of enhancing activity of a glucose-6-phosphate dehydrogenase enzyme and by means of blocking the activity of phosphoglucose isomerase.

In yet another embodiment, the present invention provides yeast cells with a modified glyoxylate shunt operational in the cytoplasm which could provide the additional reducing equivalents required to redox-balance the reductive pathway for the succinic acid pathway operational in the cytoplasm. In one aspect of this embodiment, pyruvate formate lyase is expressed in the cytoplasm to produce formate and acetyl-CoA in the cytoplasm. The formate produced from pyruvate is acted upon by formate dehydrogenase enzyme to yield NADH and CO2. In another aspect of this embodiment, the mitochondrial enzymes such as citrate synthase, isocitrate lyase and malate synthease are expressed in the cytoplasm so that there is a direct succinic acid production from the operation of a modified glyoxylate shunt in addition to the introduction of an additional reductive pathway for succinic acid production operational in the cytoplasm.

Unless otherwise defined, all terms used herein have the same meaning as commonly understood by one of ordinary skill in the art to which the invention pertains. All publications, patent applications, patents, and other references mentioned herein are incorporated by reference in their entirety. In case of conflict, the specification, including definitions and nomenclatures, will control. The materials, methods, examples, and drawings included herein are illustrative only and not intended to be limiting.

DESCRIPTION OF DRAWINGS

FIG. 1 is a diagram depicting pathways of carbon flow in a yeast cell. The outer box in this figure represents the outer membrane/cell wall of a yeast cell. The box within the yeast cell represents mitochondria. The pyruvate entering into the mitochondria combines with oxaloacetic acid (OAA) and initiates the citric acid cycle as shown with solid arrows. The carbon from the citric acid cycle also enters into the glyoxylate cycle as shown by arrows with dotted and dashed lines. There are also carboxylation reactions in the cytosol leading to the conversion of pyruvate and phosphoenolpyruvate (PEP) into oxaloacetic acid and ultimately leading to the production of succinic acid through a reductive pathway as shown by arrows with a dashed line. The fermentative pathway from pyruvate to ethanol is shown by arrows with a dotted line.

DESCRIPTION OF INVENTION

To facilitate understanding of the invention, several definitions and nomenclatures are provided herein.

A gene or coding region from a bacterium such as *E. coli* is usually named with three lower case letters in italics, sometimes followed by an upper case letter, for example "mdh" for the gene encoding malate dehydrogenase and "fumB" for the gene encoding fumarase B. The enzyme or protein encoded by a gene can be named with the same letters, but with the first letter in upper case and without italics, for example "Mdh" for malate dehydrogenase and "FumB" for fumarase B. A gene or coding region from a yeast such as *S. cerevisiae* or *K. marxianus* is usually named with three upper case letters, sometimes followed by an integer, all in italics, for example "PDC1" for a gene that encodes pyruvate decarboxylase. The enzyme or protein encoded by a gene can be named with the same letters, but with the first letter in upper case and without italics, for example "Pck" for phosphoenolpyruvate carboxykinase. The enzyme or protein can also be referred to by the more descriptive name, for example, malate dehydrogenase, fumarase B, and PEP carboxykinase for the aforementioned examples. When referring to a gene or enzyme from a particular yeast species, a pair of letters abbreviating the first letter of the genus and species can be placed in front of the gene or enzyme to designate a particular version of the gene or enzyme. For example, "ScMDH1" designates a gene encoding malate dehydrogenase isozyme 1 from *S. cerevisiae*, while "KmMDH1" designates a malate dehyhdrogenase 1 isozyme from *K. marxianus*. Note that these designations are not necessarily unique, in that any particular designation may not be limited to a particular DNA or protein sequence, since any given species can have many different strains, and different strains might have different genes or enzymes that perform the same function. In addition, a gene or coding region that encodes one example of an enzyme that possess a particular catalytic activity can have several different names because of historically different origins or because the gene comes from a different species. For brevity in this specification, and because a gene can be transferred from one microbe to another, a name consisting of three upper case letters can refer to a gene or enzyme from either a bacterium or a yeast. For example, "PCK" can refer to a phosphenolpyruvate carboxykinase or to a gene that encodes phosphenolpyruvate carboxykinase, either in or from a bacterium or in or from a yeast. Whether the three upper case designation refers to a gene or protein can be inferred from the context of the particular usage.

Any carboxylic acid or dicarboxylic acid can be referred to by either using a free acid name, such as "succinic acid", or as a salt, ester, thioester, or amide, in which case the name would be "succinate". Under physiological conditions, the free acid and the salt will both be present to some extent, so for the purposes of this invention, the two types of names shall both refer to both forms. The same shall be true for all other organic acids.

The term "expression cassette" or "cassette" means a DNA sequence that can be part of a chromosome or plasmid that contains at least a promoter and a gene or region that codes for an enzyme or other protein, such that the coding region is expressed by the promoter, and the enzyme or protein is produced by a host cell that contains the DNA sequence. An "expression cassette" can be at least partly synthetic, or constructed by genetic engineering methods, so that the coding region is expressed from a promoter that is not naturally associated with the coding region. Optionally, the "expression cassette" can contain a transcription terminator that may or may not be a terminator that is naturally associated with the coding region. An "expression cassette" can have coding regions for more than on protein, in which case, it can be called an operon, or a synthetic operon.

The term "strong constitutive promoter" means a DNA sequence that typically lies upstream (to the 5' side of a gene when depicted in the conventional 5' to 3' orientation), of a DNA sequence or a gene that is transcribed by an RNA polymerase, and that causes said DNA sequence or gene to be expressed by transcription by an RNA polymerase at a level that is easily detected directly or indirectly by any appropriate assay procedure. Examples of appropriate assay procedures include (1) quantitative reverse transcriptase plus polymerase chain reacton (PCR), (2) enzyme assay of an encoded enzyme, (3) Coomassie Blue-stained protein gel, or (4) measurable production of a metabolite that is produced indirectly as a result of said transcription, and such measurable transcription occurring regardless of the presence or absence of a protein that specifically regulates level of transcription, a metabolite, or inducer chemical. An example of a promoter that is not a "strong constitutive promoter" is the lactose operon promoter of *E. coli*, or the promoter in front of the KmLAC4 gene, since both genes are negatively regulated in the absence of an inducer such as lactose. By using well known methods in the art, a "strong constitutive promoter" can be used to replace a native promoter (a promoter that is otherwise naturally existing upstream from a DNA sequence or gene), resulting in an expression cassette that can be placed either in a plasmid or chromosome and that provides a level of expression of a desired DNA sequence or gene at a level that is higher than the level from the native promoter. A strong constitutive promoter can be specific for a species or genus, but often a strong constitutive promoter from a bacterium or yeast can function well in a distantly related bacterium or yeast, respectively. For example, a promoter from *S. cerevisiae* can function well in *K. lactis* or *K. marxianus* (Lee et al., 2012). Examples of strong constitutive promoters are promoters that drive expression of the genes that encode enzymes in a glycolytic pathway, for example ENO (enolase) or a fermentative pathway, for example PDC or alcohol dehydrogenase (ADH), genes that encode ribosomal proteins, and genes that encode translation elongation factors, for example TEF1 (Sun et al., 2012).

The term "overexpression" means of a gene or coding region means causing the enzyme or protein encoded by that gene or coding region to be produced in a host microorganism at a level that is higher than the level found in the wild type version of the host microorganism under the same or similar growth conditions. This can be accomplished by, for example, one or more of the following methods: (1) installing a stronger promoter, (2) installing a stronger ribosome binding site, (3) installing a terminator or a stronger terminator, (4) improving the choice of codons at one or more sites in the coding region, (5) improving the mRNA stability, and (6) increasing the copy number of the gene, either by introducing multiple copies in the chromosome or placing the cassette on a multicopy plasmid. An enzyme or protein produced from a gene that is overexpressed is said to be "overproduced". A gene that is being "overexpressed" or a protein that is being "overproduced" can be one that is native to a host microorganism, or it can be one that has been transplanted by genetic engineering methods from a donor organism into a host microorganism, in which case the enzyme or protein and the gene or coding region that encodes the enzyme or protein is called "foreign" or "heterologous". Foreign or heterologous genes and proteins are by definition overexpressed and overproduced, since they are not present in the unengineered host organism.

The term "plasmid" means a circular or linear DNA molecule that is substantially smaller than a chromosome, separate from the chromosome or chromosomes of a microorganism, and that replicates separately from the chromosome or chromosomes. A "plasmid" can be present in about one copy per cell or in more than one copy per cell. Maintenance of a plasmid within a microbial cell in general requires an antibiotic selection, but complementation of an auxotrophy can also be used.

Installation of the expression cassettes can be accomplished by non-homolgous, or preferably homologous, integration into the chromosome, or by installation of a replicating plasmid that contains the desired cassette(s). Assembly of more than one gene, each with its own promoter and terminator, into a package that can be manipulated as one contiguous DNA sequence for either integration into a chromosome or into a replicating plasmid, is well known in the art (Shao et al., 2012).

The term "heterologous" means a gene or protein that is not naturally or natively found in an organism, but which can be introduced into an organism by genetic engineering, such as by transformation, mating, or transduction. A heterologous gene can be integrated (inserted) into a chromosome or contained on a plasmid.

The term "exogenous" means a gene or protein that has been introduced into, or altered, in an organism for the purpose of increasing, decreasing, or eliminating an activity, by genetic engineering, such as by transformation, mating, transduction, or mutagenesis. An exogenous gene or protein can be heterologous, or it can be a gene or protein that is native to the host organism, but altered by one or more methods, for example, mutation, deletion, change of promoter, change of terminator, duplication, or insertion of one or more additional copies in the chromosome or in a plasmid. Thus, for example, if a second copy of the KmPCK gene is inserted at a site in the chromosome that is distinct from the native site, the second copy would be exogenous.

The term "homolog" means of a first gene, DNA sequence, or protein is a second gene, DNA sequence, or protein that performs a similar biological function to that of said first gene, DNA sequence or protein, and that has at statistically significant sequence identity (when comparing protein sequences or comparing a protein sequence derived from a gene sequence using the appropriate genetic code) with said first gene or protein, as determined by the BLAST computer program for sequence comparison (Saliola et al., 2004; Altschul et al., 1997; Altschul et al., 1990), and allowing for deletions and insertions. An example of a homolog of the *S. cerevisiae* gene ScURA3, which encodes orotidine-5-phosphate decarboxylase, would be the KmURA3 gene from *K. marxianus*.

The term "analog" means of a first gene, DNA sequence, or protein is a second gene, DNA sequence, or protein that performs a similar biological function to that of said first gene, DNA sequence, or protein, but where there is not statistically significant sequence identity (when comparing protein sequences or comparing the amino acid sequence derived from gene sequences) with said first gene, DNA sequence or protein, as determined by the BLAST computer program for sequence comparison (Altschul et al., 1990; Altschul et al., 1997), and allowing for deletions and insertions. For example, KmFum1p, fumarase 1 from *K. marxianus*, is an analog of FumB from *E. coli*, since they both function as fumarase, but there is no significant sequence homology between the two enzymes or their respective genes. A scientist knowledgeable in the art will know that many enzymes and proteins that have a particular biological function, for example fumarase or malate dehydrogenase, can be found in many different organisms, either as homologs or analogs, and since members of such families of enzymes or proteins share the same function, although they may be slightly or substantially different in structure, different members of the same family can in many cases be used to perform the same biological function using current methods of genetic engineering. Thus, for example, the KmFum1p fumarase from *K. marxianus* and the FumB fumarase from *E. coli* both catalyze the same reaction, so either one can result in production of fumaric acid and ultimately succinic acid in the proper context, and the choice of which one to use ultimately can be made by choosing the one that leads to a higher titer of fumaric or succinic acid under similar fermentation conditions.

The term "mutation" means any change in a DNA sequence that makes it different from a related wild type sequence. A "mutation" can comprise a single base change, deletion, insertion, replacement, frameshift, inversion, duplication, or any other type of change in a DNA sequence. The term "mutation" usually refers to a change that has a negative effect on function or reduce the activity of a gene or gene product, however, herein, the term "mutation" can also refer to a change that increases the activity of a gene or gene product. For example, a feedback resistant mutation in the aroG gene of *E. coli* increases the activity of AroG in the presence of an inhibitor such as phenylalanine. Replacement of a promoter with a different, stronger promoter, also result in a mutation that can increase the activity of a gene or gene product. The term "null mutation" means a mutation, such as a deletion of most or all of a gene, that effectively eliminates the function of a gene.

The term "mutant" means a strain or isolate that comprises one or more mutations when compared to a parent or precursor strain. A yeast mutant genotype is designated by writing the mutated gene in italicized lower case letters. For example, ura3 designates that strain comprises a mutation in the URA3 gene.

The term "genetic alteration" means any mutation, gene or DNA sequence insertion or addition, gene cassette insertion or addition, gene or DNA sequence duplication, DNA sequence deletion, whether in a host cell chromosome or in a plasmid that is installed into a host cell, that deliberately or accidentally results in a desired outcome, such as an increase or decrease in an enzyme activity, or an increase or decrease in the steady state concentration, or production, of a metabolite, when the cell resulting from said genetic alteration is compared with a related cell that does not comprise said genetic alteration. In some cases a genetic alteration will result in an increase or decrease in activity of an enzyme, in which case the desired outcome can be measured by specific activity of an enzyme activity (for example, in micromoles of substrate consumed, or product produced, per milligram of protein by whole cells, permeableized cells, a cell extract, an organelle (for example, mitochondrion) preparation, or a cell membrane preparation. In other cases, a genetic alteration will result in an increase in titer, yield, or specific productivity of a desired metabolite such as succinic acid, which can be assessed by an appropriate analytical method such as high pressure liquid chromatography (HPLC). In yet other cases, a genetic alteration will result in a decrease in titer, yield, or specific productivity of an undesired metabolite such as pyruvic acid or acetic acid.

The first step in engineering a yeast for succinate production from glucose is to create a host strain where the unwanted fermentative pathways have been deleted. In yeasts of the genera *Saccharomyces, Kluyveromyces, Candida, Pichia* and *Issatchenkia*, the predominant fermentative pathways are to ethanol (plus carbon dioxide) and glycerol. The ethanol pathway can be blocked by deleting all genes encoding pyruvate decarboxylase (PDC; EC 4.1.1.1). *Saccharomyces cerevisiae* has three such genes, ScPDC1, ScPDC5, and ScPDC6. *Kluyveromyces lactis* and *Kluyveromyces marxianus* each have only one, KlPDC1 and KmPDC1, respectively. The glycerol pathway can be blocked by deleting all genes encoding glycerol-3-phosphate dehydrogenase (EC 1.1.1.8; EC 1.1.99.5; EC1.1.1.177; EC 1.1.1.94). *S. cerevisiae* contains three such genes, GUT2, GPD1, and GPD2. *K. lactis* contains two such genes, KlGUT2 (Saliola et al., 2008) and KlGPD1 (Neves et al., 2004).

The term "major fermentation product" means a product of fermentation other than water or carbon dioxide that is produced at a concentration that is higher than any other fermentation product.

The deletion of genes may be accomplished by several methods known in the art. In one such method the DNA sequence coding for a target gene for deletion (e.g. PDC1) may be replaced by a DNA sequence coding for a gene complementing an auxotrophic marker. Commonly used markers for gene deletion and replacement include complementation of uracil, histidine, adenine, tryptophan, and leucine auxotrophies, for example in ura3, his3, ade 1, trp5, or leu2 yeast mutants. Use of these auxotrophic markers requires that first the strains are deficient in one step in the biosynthetic pathway. One commonly employed auxotrophic marker utilizes the URA3 gene. The URA3 gene when linked to a functional promoter and terminator allows the strain deficient in orotidine-5-phosphate decarboxylase (ura3) to grow on minimal media lacking uracil. Strains deficient in orotidine-5-phosphate decarboxylase can be selected by finding mutants capable of growth on 5-fluoroorotic acid (5-FOA). Strains with functional orotidine-5-phosphate decarboxylase incorporate the fluorinated compound into RNA and are not viable. In this way strains can be selected either for or against the inclusion of a functional URA3 gene. Commonly the first step involves selection on a medium lacking uracil where the presence of URA3 is required. The URA3 marker can be deleted and then reused in one or more additional rounds of genetic modification if the URA3 gene is flanked on both ends by at least one copy of the same DNA sequence, both in the same orientation, such that homologous recombination between the two flanks results in deletion of the intervening URA3 gene. This approach can be variously called the use of "tandem repeats", "tandemly repeated DNA sequences", "repetitive DNA sequences", "direct repeats", and the like. When a strain with URA3 flanked by tandem repeats is grown on 5-FOA, the URA3 gene is "looped out" or "crossed out" and can then be reused for the subsequent genetic engineering.

The cloning of the necessary genes can be achieved by any of a number of methods well known in the art, for example gene library construction in an appropriate plasmid, cosmid, phagemid, bacterial artificial chromosome, or yeast artificial chromosome, followed by screening using a DNA probe or selection by functional complementation in an appropriate mutant host cell, for example a bacterium or yeast strain. The DNA sequence for many such genes have been published and are available on the National Center for Biotechnology Information website, http://www.ncbi.nlm.nih.gov/pubmed/, for example, from *E. coli, S. cerevisiae*, and *Kluyveromyces marxianus*. For these cases, the desired gene can be amplified and cloned by polymerase chain reaction (PCR) and then cloned in an appropriate vector. To obtain the DNA sequence for a desired gene from an organism for which the DNA sequence has not yet been published, for example from *Issatchenkia orientalis* or *Kluyveromyces marxianus*, one can obtain the DNA sequence for the entire genome by well-established methods and locate the desired gene by homology to a known gene from another organism (Altschul et al., 1997; Altschul et al., 1990). Then the desired gene can be amplified by PCR and cloned in an appropriate expression vector or expression cassette. Desired DNA sequences can also be obtained by ordering synthetic fragments, for example, as "gBlocks" from Integrated DNA Technologies, Woodland, Tex., USA. DNA fragments can be joined by conventional ligation or by the "Gibson" method, using an NEBuilder kit from New England Biolabs, Ipswitch, Mass., USA.

After each desired gene is cloned, any sequence that would direct the native (wild type) protein to a subcellular organelle other than the cytoplasm can be deleted or mutated so as to substantially prevent the protein from being imported into said organelle. Methods for accomplishing this are well known in the literature. For example, it is known that the N-terminal protein sequence of a protein targeted to the mitochondrial matrix (the inner chamber of the mitochondria) can be deleted to redirect the protein to the cytoplasm. "The N-terminal targeting sequences" are also called matrix targeting sequences (MTSs) because they also bring the N terminus across the inner membrane into the matrix. In the absence of further sorting information, they direct proteins into the matrix. They have been studied in considerable detail, and their main characteristics have been known for more than 10 years. They consist of about 10-80 amino acid residues that have the potential to form amphipathic helices with one hydrophobic and one positively charged face. There is no consensus in the primary structure, which often differs considerably even between closely related orthologs. However, the general properties of these amphipathic helices are "widely conserved among fungi and animals" (Neuport and Hermann, 2007). One specific example is that the wild type fumarase encoded by the ScFUM1 gene is directed to both the mitochondria and the cytoplasm, but if the DNA sequences encoding the N-terminal 17 amino acids are deleted, then none of the enzyme is found in the mitochondria (Stein et al., 1994). An example of redirecting a peroxysomal malate dehydrogenase to the cytoplasm was accomplished by deleting the 9 base pairs encoding the C-terminal tripeptide sequence, SKL, from the MDH3 gene (Zelle et al., 2008). In addition to deleting or mutating any organelle targeting sequence, the gene for each desired enzyme can be functionally coupled to a constitutive promoter. In a preferred embodiment, each of the desired genes is couple to a different promoter, so that the individual gene expression cassettes can be assembled together in one pathway cassette without having any substantially repeated DNA sequences in the pathway cassette, which in turn makes it more convenient to integrate the assembled pathway cassette into a chromosome of the intended host strain or into a plasmid as a vehicle for introducing the pathway cassette. After the pathway cassette is assembled, it is installed in the host strain described above.

Installation of expression cassettes can be accomplished by non-homolgous, or preferably homologous, integration into the chromosome, or by installation of a replicating plasmid that contains the desired cassette(s). Optionally, installation of an expression cassette can be combined with deletion of one or more of the unwanted genes, for example KmPDC1, such that the cassette substitutes for the unwanted gene, in effect accomplishing two of the desired steps at once. The promoter of the unwanted gene can be arranged to be used to drive expression of one of the desired genes. For example, integration of a cassette designed to give expression of the E. coli pck gene at the KmPDC1 locus can be designed so that the pck open reading frame precisely replaces the KmPDC1 open reading fame. If more than one gene are to be expressed from the cassette, then it can be arranged so that the last gene of the array is functionally coupled to the KmPCD1 terminator.

The term "succinic acid biosynthetic pathway" means any series of enzymatic, and optionally non-enzymatic, chemical reactions that begin with one or more carbon sources, such as a sugar or glycerol, and leads ultimately to succinic acid.

Figure 1:
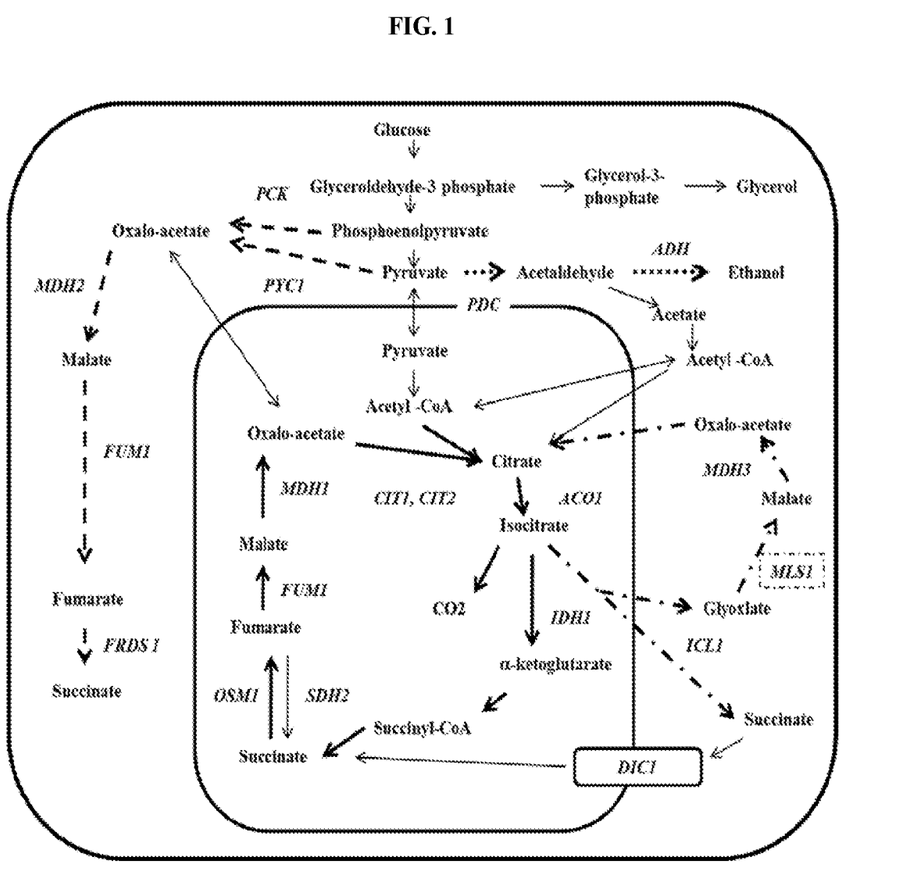

There are three traditional succinic acid biosynthetic pathways: the reductive TCA branch, the oxidative TCA branch, and the glyoxylate shunt (FIG. 1). A fourth, novel pathway, involving a malic enzyme, is one of the aspects of this patent. A "malic enzyme" is an enzyme that converts pyruvate directly to malate by the addition of carbon dioxide and a reducing equivalent, bypassing oxaloacetate as an intermediate. There are two versions of malic enzyme found in nature. The first version is named an "NADH-dependent malic enzyme", also referred to as EC 1.1.1.39 and EC 1.1.1.38, which prefers NADH over NADPH as its co-factor. In other words, the enzyme has a higher affinity (lower $K_m$) for NADH than for NADPH, or it is capable of achieving a higher $V_{max}$ when using NADH as a cosubstrate than when using NADPH as a cosubstrate. The second version is named an "NADPH-dependent malic enzyme", also referred to as EC 1.1.1.40, which prefers NADPH over NADH as its co-factor. In other words, the enzyme has a higher affinity (lower $K_m$) for NADPH than for NADH, or it is capable of achieving a higher $V_{max}$ when using NADPH as a cosubstrate than when using NADH as a cosubstrate.

Figure 2:
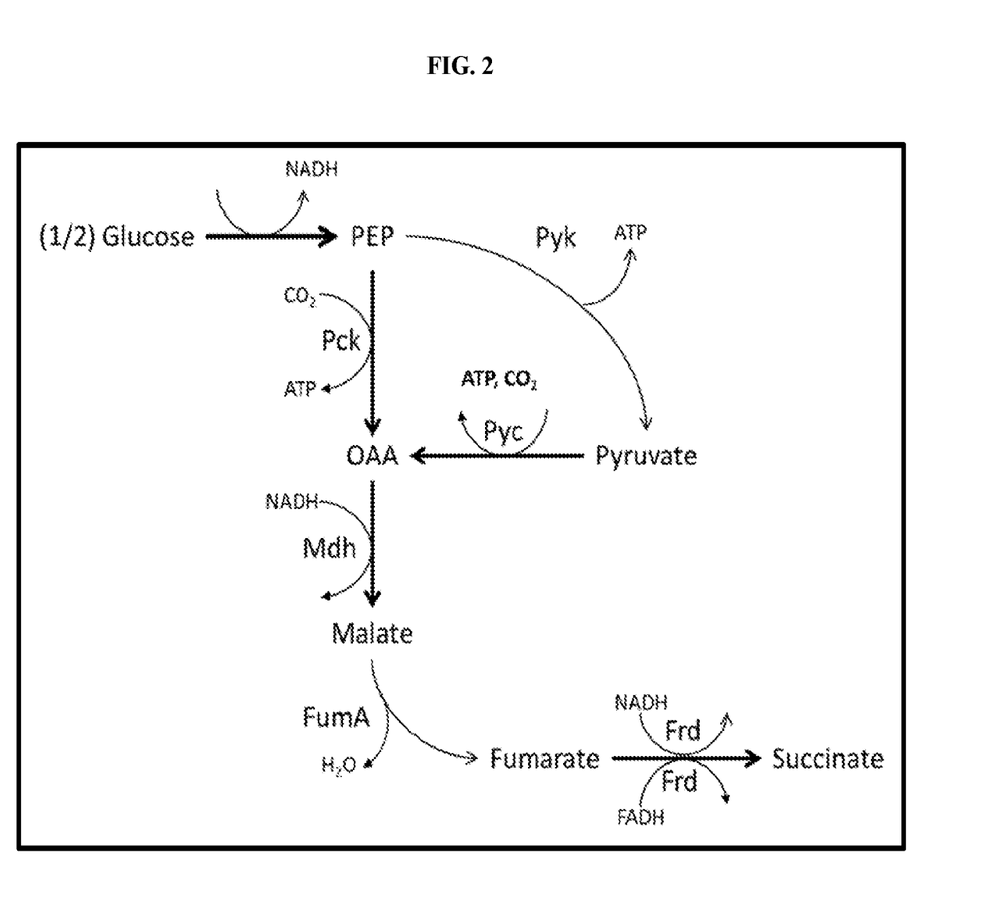
FIG. 2 is a diagram depicting the reductive pathway for succinic acid production in the yeast cells. Phosphoenolpyruvate (PEP) is carboxylated by a phosphoenol pyruvate carboxykinase (Pck) enzyme to yield a molecule of oxaloacetate (OAA). When a molecule of oxaloacetate is converted into a molecule of succinate, two reducing equivalents are consumed. PEP can also be acted upon by pyruvate kinase to yield pyruvate which can be carboxylated by pyruvate carboxylase to yield oxaloacetate.

The reductive TCA branch (the reductive pathway for succinate production) starts with the carboxylation of either phosphoenol pyruvate (PEP) or pyruvate to yield oxaloacetate (FIG. 2). The carboxylation of PEP may be done by either of the enzymes phosphoenolpyruvate carboxylase (PPC) or phosphoenolpyruvate carboxykinase (PCK). The use of the PCK enzyme is preferred in a succinate producing pathway since one adenosine triphosphate (ATP) is generated together with oxaloacetate. The carboxylation of pyruvate can be achieved by pyruvate carboxylase (PYC). Oxaloacetate is reduced to malate by malate dehydrogenase (MDH). Malate is converted to fumarate by fumarase (FUM). Finally, succinate is produced from fumarate by fumarate reductase (FRD). The reductive TCA branch is a high yielding pathway, but it is a net consumer of reducing equivalents in the form of NADH, NADPH, and/or FADH. The term "reducing equivalent" means a chemically reduced form of hydrogen that is carried by a redox cofactor and can be used by an enzyme to chemically reduce a substrate. For example, NADH is the reduced form of nicotinamide adenine dinucleotide, which can donate its reduced hydrogen atom to fumarate to form succinate, catalyzed by the enzyme fumarate reductase. In such a reaction, the cofactor becomes converted to the oxidized form, in this example NAD, which then needs to be recycled back to the reduced form to function in a succinic acid biosynthetic pathway. The term "redox cofactor" means any compound that is used as co-substrate in an enzymatic reaction to donate a reducing equivalent to another substrate, or receive a reducing equivalent from another substrate. Redox co-factors exist in pairs of reduced and oxidized forms. Examples of such pairs include, but are not limited to, NADH/NAD (sometimes written as $NAD^+$), NADPH/NADP (sometimes written as $NADP^+$), FAD/FADH (sometimes written as $NADH_2$), and FMN/FMNH (sometimes written as $FMNH_2$). The term "reducing cofactor" means the chemically reduced form of a redox cofactor, for example NADH, NADPH, FADH, or FMNH. During glycolysis, one reducing equivalent is produced (NADH) during PEP production, but two reducing equivalents (e.g. NADH, NADPH, and/or FADH) are needed for the conversion of PEP to succinate. The process of providing the required level of reducing equivalents for the operation of reductive pathway for succinic acid production in the cytoplasm using the reducing equivalents generated from oxidative succinic acid pathway or glyoxylate succinic acid pathway is referred as redox balancing the reductive pathway for succinic acid production in the cytoplasm.

Both the oxidative TCA branch and the glyoxylate shunt provide lower yielding pathways to succinate than the reductive TCA branch, but either can provide the additional reducing equivalents needed to achieve redox balance for succinate biosynthesis via the reductive pathway from glucose or other carbohydrate carbon sources under anaerobic or microaerobic conditions. The oxidative TCA branch (oxidative production of succinic acid) begins with citrate synthase (CIT) forming citrate from acetyl-CoA and oxaloacetate. Citrate is converted to isocitrate by aconitase (ACN). Isocitrate dehydrogenase (IDH) converts isocitrate to ?-ketoglutarate, which is further converted to succinyl-CoA by alpha-ketoglutarate dehydrogenase (KGD). Succinate is then produced from succinyl-CoA by succinyl-CoA synthetase (SCS) or succinate thiokinase or succinate-CoA ligase. Succinate-CoA ligase is an enzyme that catalyzes the reversible reaction of succinyl-CoA to succinate. For each succinate produced via the oxidative TCA branch, five reducing equivalents are produced. During the operation of the glyoxylate shunt (gyloxylate pathway for succinic acid production) isocitrate is split into succinate and glyoxylate by isocitrate lyase (ICL). Malate Synthase (MLS) forms malate from glyoxylate and acetyl-CoA. Malate is then converted to fumarate and then succinate. The maximum reducing equivalents produced via the glyoxylate shunt are eight reducing equivalents for every four succinate molecules produced from three glucose molecules.

Redox balancing of a reductive pathway for succinate production in the cytoplasm with the reducing equivalents generated from the operation of an oxidative pathway for succinate production, such as the oxidative direction of the TCA cycle or a glyoxylate pathway, is not easy to achieve, so there is still a need for identifying pathways within the yeast cells that could supply reducing equivalents needed for the operation of the reductive pathway for succinic acid production in the cytoplasm. Additional routes for succinate production need to produce sufficient reducing equivalents.

Figure 3:
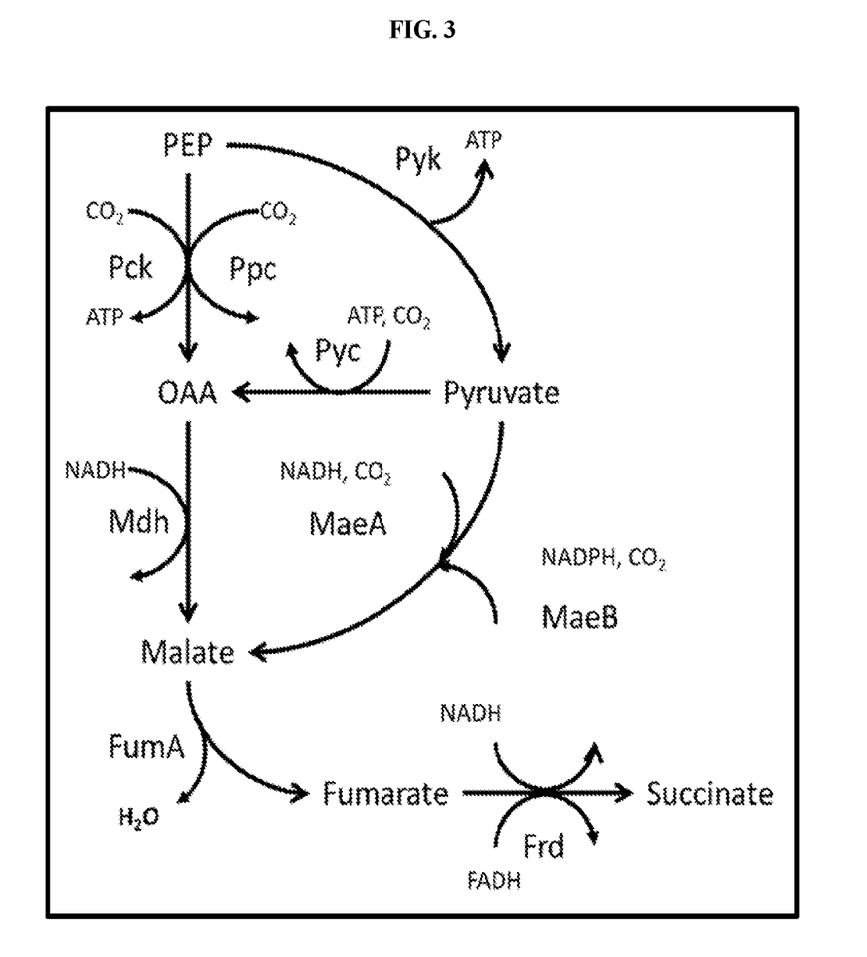
FIG. 3 is a diagram depicting the pathway for production of malate in the cytoplasm from phosphoenolpyruvate (PEP). Pyruvate kinase (Pyk) acts upon PEP to yield pyruvate, which is acted upon either by an NADH-dependent malic enzyme or an NADPH-dependent malic enzyme in the presence of carbon dioxide to yield malate, which can enter into the reductive pathway.

One alternative source for reducing equivalents is the pentose phosphate pathway (PPP). The pentose phosphate pathway is a source of reducing equivalents (NADPH) as well as a source of carbon dioxide and five carbon sugar phosphates required for the synthesis of nucleotides. After glucose enters the cell and is phosphorylated to glucose-6-phosphate, the oxidative PPP converts glucose-6-phosphate to ribulose-5-phosphate along with two molecules of NADPH and one $CO_2$ by the enzymes glucose-6-phosphate dehydrogenase (G6PD or ZWF), 6-phosphogluconolactonase (SOL or PGL), and 6-phosphogluconate dehydrogenase (GND). By increasing the activity of glucose-6-phosphate dehydrogenase and/or 6-phosphogluconolactonase (PGL) and/or 6-phosphogluconate dehydrogenase (GND), and/or by decreasing the activity of glucose-6-phosphate isomerase (PGI) one can direct an increase in carbon flux through the PPP, generating the required reducing equivalents necessary for balancing the reductive TCA branch for succinate production (FIG. 3). PGI can be reduced in activity or completely inactivated through a gene deletion or other mutation thereby forcing the entire carbon flux from glucose through the PPP. A PGI deletion causes an elimination of growth on glucose in *Saccharomyces cerevisiae*, but in other microorganisms (e.g. the bacterium *E. coli* or the yeast *Kluyveromyces lactis*) a PGI deletion is tolerated. Generally cellular growth is hindered in these PGI deficient strain backgrounds, at least initially. PGI mutants have been studied and faster growing mutants have been characterized (Sekar et al., 2017). To restore partial or full growth compared to the wild type strains, cells need to utilize the excess reducing equivalents produced via the PPP. In *E. coli*, NADPH can be converted to NADH, which is more readily used by the cell for succinate biosynthesis. Evolved strains frequently harbor mutations in either the soluble or the membrane-bound transhydrogenase that allows for the interconversion of these reducing equivalents. In addition, increased flux into the PPP by increasing ZWF activity has been shown to improve growth rates of PGI deficient strains (Sekar et al., 2017). Thus, in one embodiment, flux through the PPP from glucose-6-phosphate to glyceraldehyde-3-phosphate and fructose-6-phosphate is enhanced by one or more genetic alterations that increases the activity of one or more enzymes of the PPP and/or blocking or reducing flux directly through the Embden-Meyerhof-Parnas pathway by decreasing or eliminating phosphoglucose isomerase (PGI) activity. Enzymes of the PPP include glucose-6-phosphate dehydrogenase (ZWF), 6-phosphogluconolactonase (PGL), 6-phosphogluconate dehydrogenase (GND), transketolase (TKT), transaldolase (TAL), ribulose-5-phosphate epimerase (RPE), and ribulose-5-phosphate isomerase (RPI).

Figure 4:
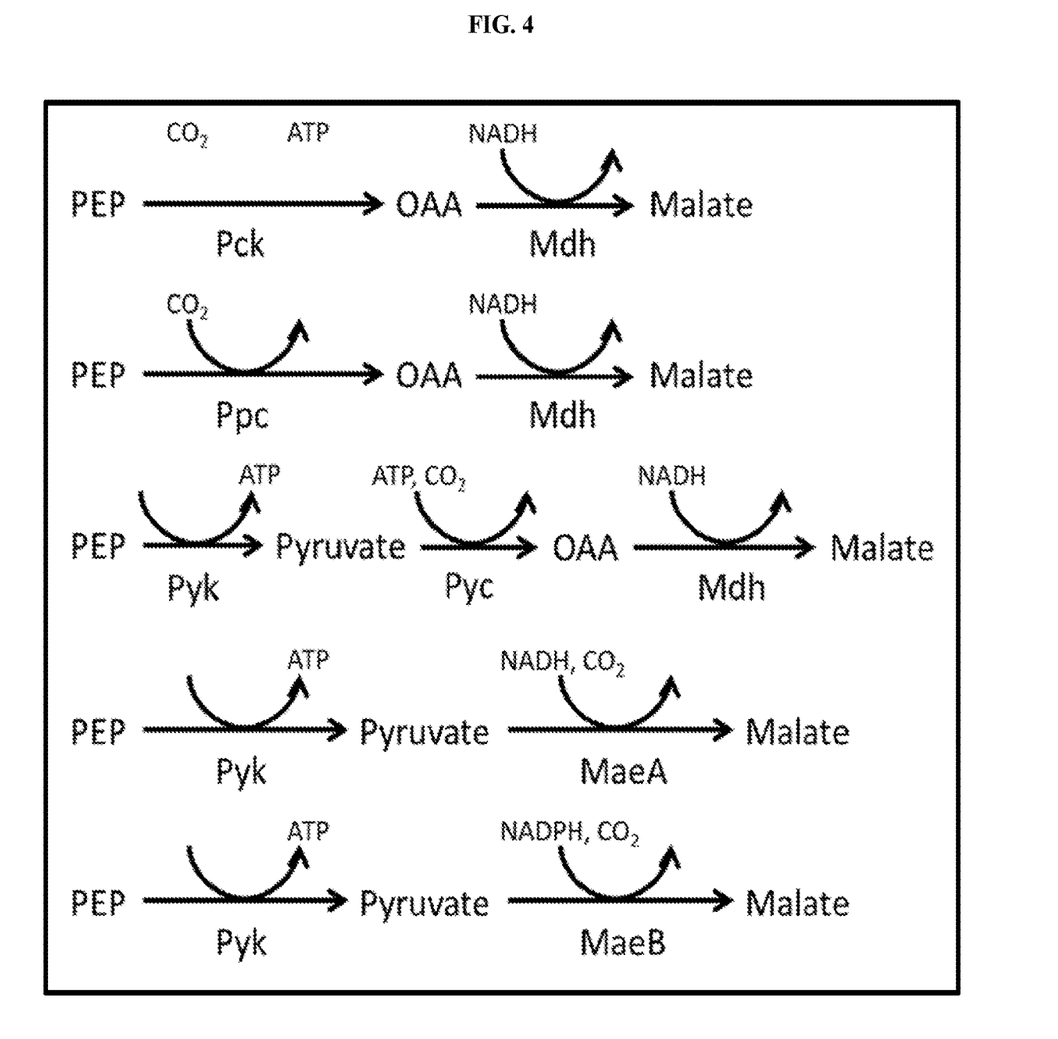
FIG. 4 is a diagram depicting the pathways for the production of malate from PEP in the cytoplasm. Phosphoenolpyruvate (PEP) is carboxylated by pyruvate kinase (Pck) or phosphoenolpyruvate carboxylase (Ppc) to yield oxaloacetate acid, which is reduced by malate dehydrogenase using NADH to yield malate. PEP can also be acted upon by Pyk to yield pyruvate which can be carboxylated to obtain oxaloacetate, which in turn can be reduced to malate. In addition, pyruvate can be carboxylated either by an NADH depended malic enzyme or an NADPH-dependent malic enzyme to yield malate. Irrespective of the path of production, malate acts as the starting point for the reductive pathway for succinic acid production in the cytoplasm of the yeast cell.
Figure 5:
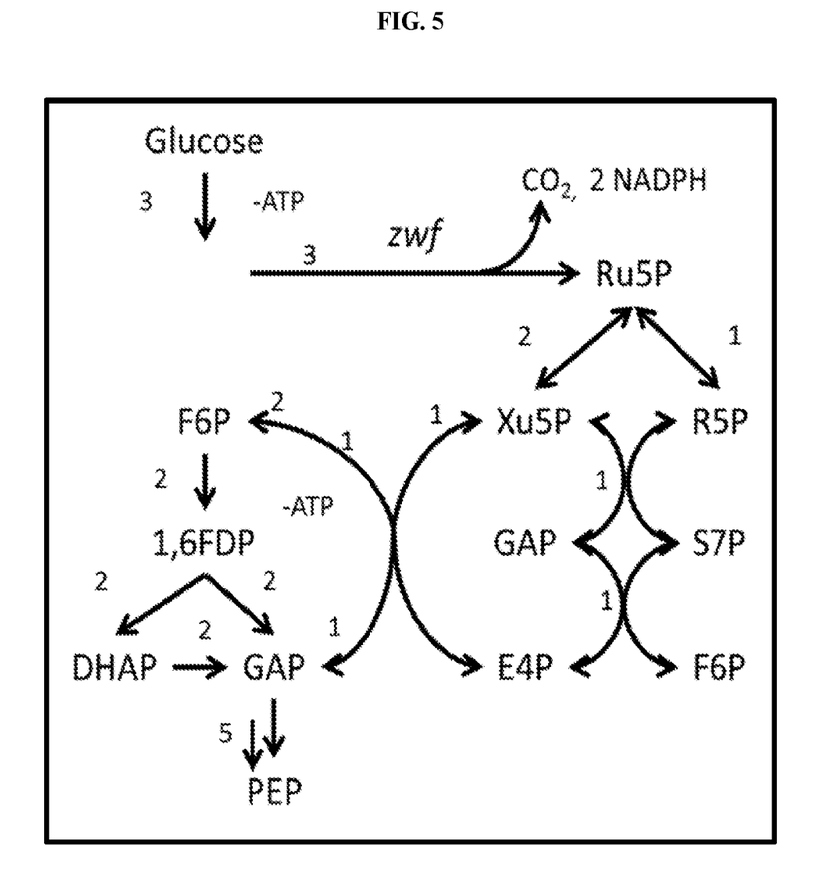
FIG. 5 is a diagram depicting the flow of carbon through the pentose phosphate pathway. Glucose-6-phosphate (glucose) is subjected to glucose-6-phosphate dehydrogenase (ZWF) to produce ribulose-5-phosphate (Ru5P). In the normal course of glycolytic reactions within the yeast cell, glucose-6-phosphate is converted into glucose-1-phosphate by a phosphoglucose isomerase enzyme (not depicted). In order to enhance the flow of carbon into the pentose phosphate pathway, the activity of ZWF is increased while the activity of phosphoglucose isomerase enzyme activity is decreased or inhibited.
Figure 6:
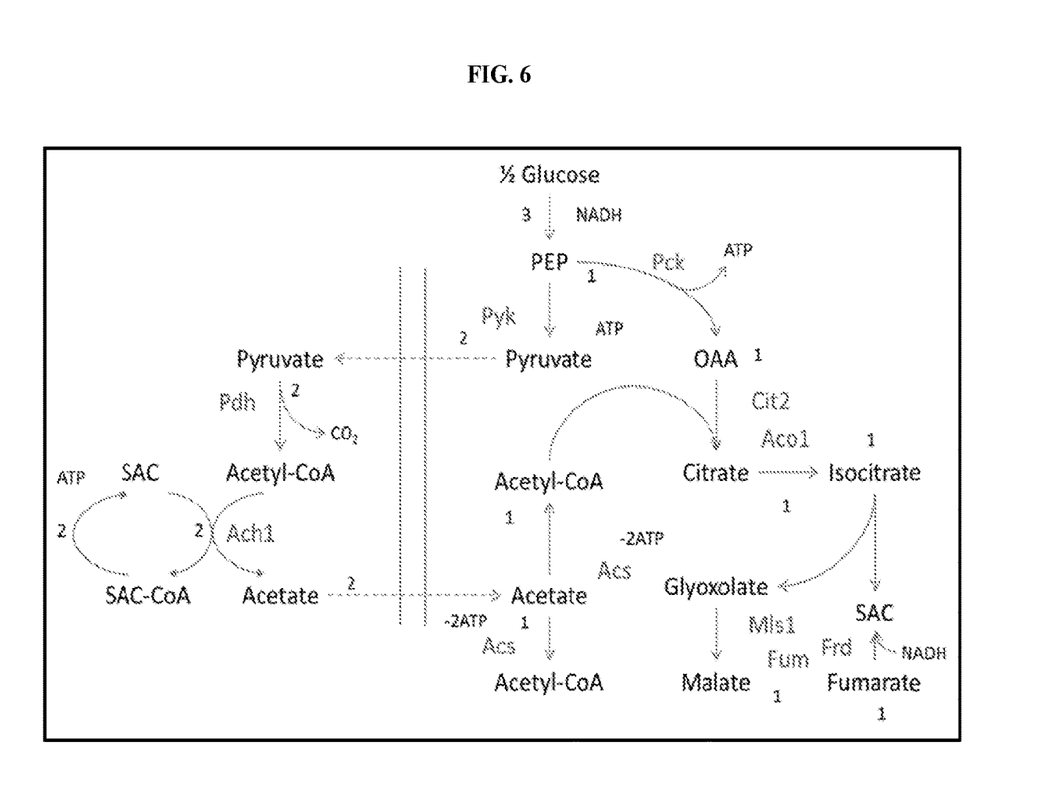
FIG. 6 is a diagram depicting the flow of pyruvate and acetate across the mitochondrial membrane shown in this figure as two vertical lines. Pyruvate from glycolysis in the cytoplasm enters the mitochondria through simple diffusion. Pyruvate is decarboxylated to yield acetyl-CoA, which is used to produce succinyl-CoA and acetate. The acetate diffuses out of the mitochondria through simple diffusion and is acted upon by acetyl CoA synthase to yield acetyl-CoA which in turn combines with oxaloacetate to acid yield citrate. Citrate enters into the glyxoylate shunt to yield glyoxylate and succinate (SAC). The area to the left of the two vertical lines represents the mitochondria and the area to the right of the two vertical lines represents the cytoplasm.
Figure 7:
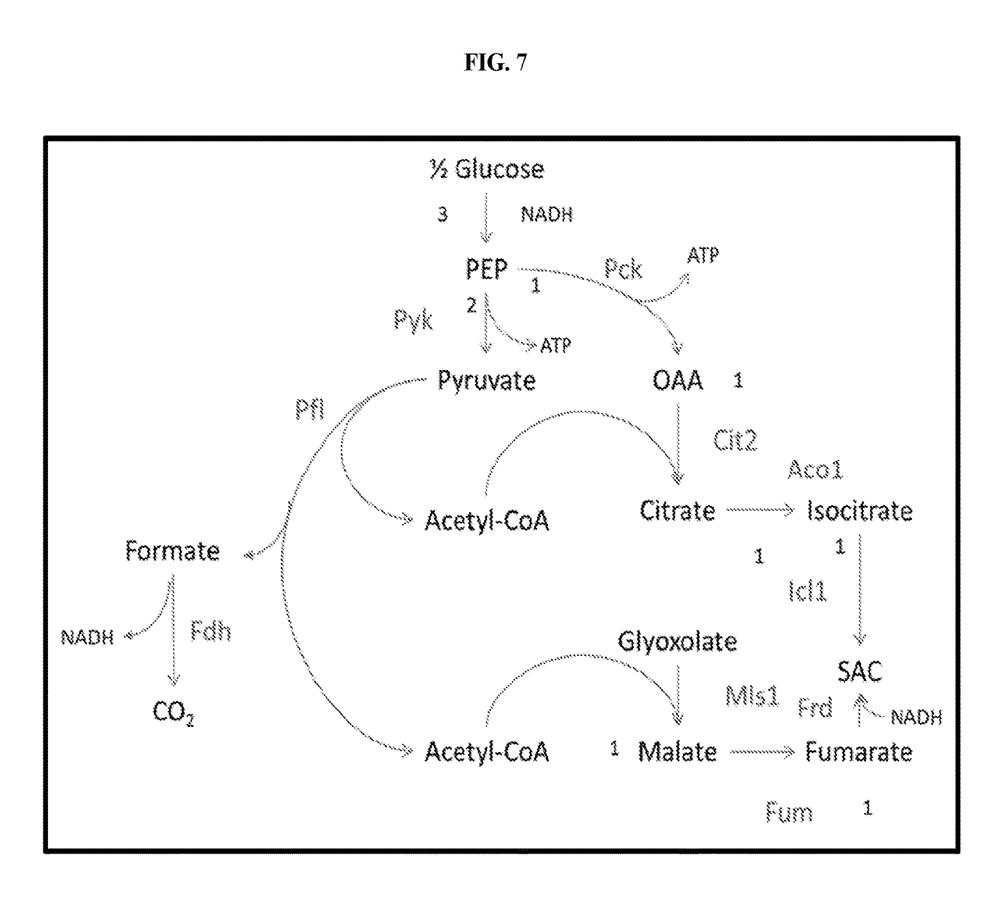
FIG. 7 is a diagram depicting the formation of acetyl CoA in the cytoplasm. Pyuruvate formate lyase (PFL) acts on pyruvate to yield formate and acetyl-CoA. Formate is acted upon by formate dehydrogenase to yield carbon dioxide and NADH. Acetyl-CoA reacts with oxaloacetate acid to yield citric acid which, isomerizes to yield isocitrate, which in turn is split into glyoxylate and succinate. Glyoxylate and acetyl-CoA combine together to yield malate, which is ultimately converted into succinic acid.

As mentioned previously, the glyoxylate shunt is commonly utilized as a source for reducing equivalents during succinate production, but particularly in yeast this pathway suffers from considerable limitations. In yeast engineered for the production of products other than ethanol, the pyruvate decarboxylase (PDC) is responsible for undesirable byproducts, acetaldehyde and ethanol. The elimination of pyruvate decarboxylase from yeast also eliminates the only fully cytosolic source of acetyl-CoA. In PDC deficient strain backgrounds pyruvate must be transported into the mitochondrion and converted to acetyl-CoA by pyruvate dehydrogenase (PDH). Acetyl-CoA is then converted to acetate inside the mitochondrion and then transported back to the cytosol where acetyl-CoA synthase (ACS) can convert acetate to acetyl-CoA. Not only is this circuitous route inefficient, it also results in higher energy expenditure by the cell. Acetyl-CoA produced by ACS utilizes ATP and results in AMP, requiring considerable more energy than the formation of acetyl-CoA via the traditional route. A common bacterial route to acetyl-CoA relies on pyruvate formate lyase (PFL). PFL converts pyruvate to acetyl-CoA and formate. Formate can be further oxidized to CO2 by formate dehydrogenase (FDH) producing reducing equivalents needed for succinate production. PFL requires both the catalytic protein and an activating enzyme. PFL is known to be an oxygen sensitive enzyme requiring re-activation for activity. Previous groups have expressed PFL in *S. cerevisiae* and shown that it is capable of producing the acetyl-CoA needed by the cell in place of the native pathways. Further studies have shown that the co-expression of ferredoxins can significantly improve the oxygen tolerance of the enzyme when expressed in yeast (Zhang et al., 2015). The acetyl-CoA produced from PFL can be utilized by the enzymes in the glyoxolate shunt and the reducing equivalents formed by FDH can be used in the reductive TCA branch (FIGS. 4 and 5).

EXAMPLES

Example 1

Installation of the Reductive TCA Branch

In yeast, the enzymes involved in the TCA cycle are targeted to the mitochondrion. Glycolysis up to pyruvate and oxaloacetate production occurs in the cytoplasm. In order to have an optimal succinate production route, it is preferred to have all necessary enzymes in the cytoplasm. For a cytoplasmic reductive TCA branch the MDH, FUM, and FRD enzymes should all be localized to the cytoplasm. This can be achieved by expressing bacterial genes that lack a mitochondrial targeting sequence, or by eliminating the mitochondrial target sequence found in yeast proteins. Additionally, increased PCK activity is also desired to produce a more energetically favorable route to succinate. High activity of MDH, FUM, FRD, and PCK can be achieved by linking the expression of the genes with high strength promoters. Examples of such high strength promoters include, but are not limited to, PDC, TDH (triose phosphate dehydrogenase), ENO (enolase), TPI (triose phosphate isomerase), TEF (translation elongation factor), ADH (alcohol dehydrogenase), and GDP (glycerol-3-phosphate dehydrogenase). Generally promoters of genes involved in glycolysis are strong constitutively expressed promoters and are good choices for gene overexpression.

Installation of the expression cassettes can be accomplished by non-homolgous, or preferably homologous, integration into the chromosome, or by installation of a replicating plasmid that contains the desired cassette(s). Integration sites in the genome can be done at loci containing genes of unwanted byproducts, such as PDC or ADH involved in ethanol formation, or GPP and GDP involved in glycerol formation. Assembly of more than one gene, each with its own promoter and terminator, into a package that can be manipulated as one contiguous DNA sequence for either integration into a chromosome or into a replicating plasmid, is well known in the art (Shao et al., 2012).

Example 2

Succinate Pathway with Increased Flux Through the Pentose Phosphate Pathway and Elimination or Reduction of PGI Activity Once the host strain has been constructed with expression of the reductive TCA branch, additional reducing equivalents are needed for a high yielding succinate pathway. One way that additional reducing equivalents can be produced is by the redirection of carbon flux through the pentose phosphate pathway (PPP). At least a partial redirection can be achieved by increasing the activity of glucose-6-phosphate dehydrogenase (ZWF) using methods for overexpression described earlier. A more complete redirection of carbon can be achieved by the decreasing or deletion of glucose-6-phosphate isomerase (PGI) activity. The deletion results in the highest production of NADPH through the PPP when growing on glucose. In another embodiment, both an increase in ZWF, PGL, and/or GND activity, and an elimination or reduction in glucose-6-phosphate isomerase is engineered into the same cell.

In one embodiment the PGI DNA sequence is replaced by the URA3 gene flanked by direct repeats. In a second step, upon selection using 5-FOA, the URA3 marker is removed. In another embodiment the PGI DNA sequence is not only removed but is replaced with the DNA sequence that codes for glucose-6-phosphate dehydrogenase. This not only directs flux into the PPP by elimination of PGI, but increases ZWF activity in a single step. Another embodiment allows use the NADPH produced by the PPP for malate, fumarate, or succinate production by the introduction of, or the increase in activity of, a malic enzyme. The malic enzyme can be one that prefers NADPH or one that prefers NADH as a substrate. A malic enzyme that prefers NADPH, in other words, a malic enzyme that has a lower Km for NADPH than for NADH, or one that has a higher Vmax with NADPH compared to NADH, shall be referred to for brevity herein and in the claims as an "NADPH-dependent malic enzyme". In a preferred embodiment, the malic enzyme prefers NADPH as a substrate, since NADPH is the form of reducing equivalent that is produced by the PPP. One example of a gene that encodes this activity is the maeB gene of *E. coli*. The malic enzyme (MaeB) carboxylates pyruvate utilizing one NADPH, producing malate. The malate produced is then further converted to succinate by MDH, FUM, and FRD.

In another embodiment, the cell is engineered to have an increase in activity of a malic enzyme that prefers NADH, in other words, a malic enzyme that has a lower Km for NADH than for NADPH, or one that has a higher Vmax with NADH compared to NADPH, which shall be referred to for brevity herein and in the claims as an "NADH-dependent malic enzyme". One example of a gene that encodes this activity is the maeA or sfcA gene of *E. coli*. The malic enzyme (MaeA) carboxylates pyruvate producing NADH and malate. The malate produced can then be further converted to fumarate and/or succinate by MDH, FUM, and FRD.

Example 3

Exogenous Route to Acetyl-CoA by PFL

Reducing equivalents needed for balancing the reductive TCA branch can also be generated by running the glyoxolate shunt. Natively, the glyoxolate shunt provides a way for cells to grow on acetate or 2-carbon units as a sole carbon source. The glyoxolate shunt begins with the formation of citrate from acetyl-CoA and oxaloacetate by citrate lyase (CIT). Then, isocitrate is produced from citrate by aconitase (ACO). Isocitrate lyase (ICL) converts isocitrate into glyoxolate and succinate. Malate synthase (MLS) condenses acetyl-CoA and glyoxylate to form malate. The malate produced is then further converted to succinate by FUM and FRD. Cytosolic acetyl-CoA is normally produced in yeast via PDC. However, in yeast engineered for products other than ethanol, the PDC is typically inactivated. This presents the cell with the difficulty of producing cytosolic acetyl-CoA. This can be achieved by utilizing mitochondrially produced acetate and transporting this into the cytoplasm and then converting the acetate into acetyl-CoA, although this requires the conversion of ATP into AMP, a costly reaction in cellular energetics. A more favorable biochemical route both in term of energy use (e.g. ATP) and reduction potential utilizes pyruvate formate lyase (PFL) and formate dehydrogenase (FDH). PFL requires two polypeptides for functionality, PflA and PflB. PflA is an activating enzyme generating a glycyl radical in the catalytic enzyme PflB. PFL is not native to any known yeast, but previous research has shown that PFL can be functionally expressed in yeast. One potential issue is that PFL is known as an anaerobic enzyme, and depending on culture conditions (e.g. high aeration), PFL could be inactivated. Recent research has shown that through the overexpression of flavodoxin or ferredoxin together with their respective partner reductases, aerobic functionality of PFL in yeast could be enhanced. "Flavodoxin" and "ferredoxin" refer to any of a number of small proteins that act in redox reactions, and which can function to increase the specific activity of a PFL by activation, reactivation, or protection form oxidation. A functional PFL would generate acetyl-CoA that can enter the glyoxylate shunt pathway, and also formate. The formate can be further converted to $CO_2$ by formate dehydrogenase, while also generating one NADH to further enhance the available reducing power of this pathway. One the host strain has been engineered to express a cytosolic reductive TCA branch, the four enzymes necessary for the glyoxolate shunt (CIT, ACO, ICL, and MLS) can also be expressed in the cytoplasm using methods described earlier. To this strain the pflA and plfB genes from *E. coli* can be introduced either on the chromosome or on plasmids. Additionally the ferrodoxin or flavodoxin and their associated partner oxido-reductase, for example fdxB and CG0639 from *Corynebacterium glutamicum* ATCC 13032 or fldA and fpr from *E. coli* K-12, can also be added and/or over-expressed if needed to increase the activity of PFL or protect it from inactivation. Finally, FDH (formate dehydrogenase) can be added or increased in activity by installing a gene from *S. cerevisiae*, or a bacterial source. A strain engineered to produce succinate that comprises an added or increased formate dehydrogenate activity can optionally be fed formate in addition to glucose in order to provide reducing equivalents for a reductive succinate pathway in the form of NADH.

A strain that is engineered to provide oxaloacetate by use of a malic enzyme and reducing equivalents from the PPP can optionally be engineered to reduce or eliminate pyruvate carboxylase (PYC) activity in order to force the cell to rely more heavily on the malic enzyme pathway for oxaloacetate biosynthesis.

REFERENCES

Abbott, D. A., Zelle, R. M., Pronk, J. T. and van Maris, A. J. A. (2009) Metabolic engineering of *Saccharomyces cerevisiae* for production of carboxylic acid: current status and challenges. FEMS Yeast Res. 9, 1123-1136.

Abdel-Banat, B. M., Nonklang, S., Hoshida, H., and Akada, R. (2010) Random and targeted gene integrations through the control of non-homologous end joining in the yeast *Kluyveromyces marxianus*, Yeast 27, 29-39.

Altschul, S. F., Gish, W., Miller, W., Myers, E. W., and Lipman, D. J. (1990) Basic local alignment search tool, J Mol Biol 215, 403-410.

Altschul, S. F., Madden, T. L., Schaffer, A. A., Zhang, J., Zhang, Z., Miller, W., and Lipman, D. J. (1997) Gapped BLAST and PSI-BLAST: a new generation of protein database search programs, Nucleic Acids Res 25, 3389-3402.

Anderlund, M., Nissen, T. L., Nielsen, J., Villadsen, J., Rydstrom, J., Hahn-Hagerdal, B., and Kielland-Brandt, M. C. (1999) Expression of the *Escherichia coli* pntA and pntB genes, encoding nicotinamide nucleotide transhydrogenase, in *Saccharomyces cerevisiae* and its effect on product formation during anaerobic glucose fermentation, Appl Environ Microbiol 65, 2333-2340.

Avalos, J. L., fink, G. R., and Stephanopoulos, G. (2013) Compartmentalization of metabolic pathways in yeast mitochondria improves the production of branched-chain alcohols. Nat Biotechnol 31, 335-341.

Booth, L. N., Tuch, B. B., and Johnson, A. D. (2010) Intercalation of a new tier of transcription regulation into an ancient circuit, Nature 468, 959-963.

Camarasa, C., Faucet, V., and Dequin, S. (2007) Role in anaerobiosis of the isoenzymes for *Saccharomyces cerevisiae* fumarate reductase encoded by OSM1 and FRDS1, Yeast 24, 391-401.

Cao, Z., Song, P., Xu, Q., Su, R., and Zhu, G. (2011) Overexpression and biochemical characterization of soluble pyridine nucleotide transhydrogenase from *Escherichia coli*, FEMS Microbiol Lett 320, 9-14.

Coves, J., Niviere, V., Eschenbrenner, M., and Fontecave, M. (1993) NADPH-sulfite reductase from *Escherichia coli*. A flavin reductase participating in the generation of the free radical of ribonucleotide reductase, J Biol Chem 268, 18604-18609.

Cox, S. J., Shalel levanon, S., Sanchez, A., Lin, H., Peercy, B., Bennett, G. N., and San, K. Y.

(2006) Development of a metabolic network design and optimization framework incorporating implementation constraints: a succinate production case study. Metab Eng 8, 46-57.

de Klerck, J.-L. (2010) Succinic acid production by wine yeasts, in Department of Citiculture and Oenology, pp. 1-156, Stellenbosch University.

Dujon, B., Sherman, D., Fischer, G., Durrens, P., Casaregola, S., Lafontaine, I., De Montigny, J., Marck, C., Neuveglise, C., Talla, E., Goffard, N., Frangeul, L., Aigle, M., Anthouard, V., Babour, A., Barbe, V., Barnay, S., Blanchin, S., Beckerich, J. M., Beyne, E., Bleykasten, C., Boisrame, A., Boyer, J., Cattolico, L., Confanioleri, F., De Daruvar, A., Despons, L., Fabre, E., Fairhead, C., Ferry-Dumazet, H., Groppi, A., Hantraye, F., Hennequin, C., Jauniaux, N., Joyet, P., Kachouri, R., Kerrest, A., Koszul, R., Lemaire, M., Lesur, I., Ma, L., Muller, H., Nicaud, J. M., Nikolski, M., Oztas, S., Ozier-Kalogeropoulos, O., Pellenz, S., Potier, S., Richard, G. F., Straub, M. L., Suleau, A., Swennen, D., Tekaia, F., Wesolowski-Louvel, M., Westhof, E., Wirth, B., Zeniou-Meyer, M., Zivanovic, I., Bolotin-Fukuhara, M., Thierry, A., Bouchier, C., Caudron, B., Scarpelli, C., Gaillardin, C., Weissenbach, J., Wincker, P., and Souciet, J. L. (2004) Genome evolution in yeasts, Nature 430, 35-44.

Easlon, E., Tsang, F., Skinner, C., Wang, C., and Lin, S. J. (2008) The malate-aspartate NADH shuttle components are novel metabolic longevity regulators required for calorie restriction-mediated life span extension in yeast, Genes Dev 22, 931-944.

Eschenbrenner, M., Coves, J., and Fontecave, M. (1995) The flavin reductase activity of the flavoprotein component of sulfite reductase from *Escherichia coli*. A new model for the protein structure, J Biol Chem 270, 20550-20555.

Galan, B., Manso, I., Kolb, A., Garcia, J. L., and Prieto, M. A. (2008) The role of FIS protein in the physiological control of the expression of the *Escherichia coli* meta-hpa operon, Microbiology 154, 2151-2160.

Grabar, T. B., Zhou, S., Shanmugam, K. T., Yomano, L. P., and Ingram, L. O. (2006) Methylglyoxal bypass identified as source of chiral contamination in l(+) and d(−)-lactate fermentations by recombinant *Escherichia coli*, Biotechnol Lett 28, 1527-1535.

Heerde, E., and Radler, F. (1978) Metabolism of the Anaerobic Formation of succininc acid by *Saccharomyces cerevisiae*. Archives of Microbiology 117, 269-276.

Heinisch, J. J., Buchwald, U., Gottachlich, A., Heppler, N., and Rodicio, R. (2010) A tool kit for molecular genetics of *Kluyveromyces lactis* comprising a congenic strain series and a set of versatile vectors. FEMS Yeast Res 10, 333-342.

Hurt, E. C., Allison, D. S., Muller, U., and Schatz, G. (1987) Amino-terminal deletions in the presequence of an imported mitochondrial protein block the targeting function and proteolytic cleavage of the presequence at the carboxy terminus. J Biol chem. 262, 1420-1424.

Jantama, K., Haupt, M. J., Svoronos, S. A., Zhang, X., Moore, J. C., Shanmugam, K. T., and Ingram, L. O. (2008a) Combining metabolic engineering and metabolic evolution to develop nonrecombinant strains of *Escherichia coli* C that produce succinate and malate, Biotechnol Bioeng 99, 1140-1153.

Jantama, K., Zhang, X., Moore, J. C., Shanmugam, K. T., Svoronos, S. A., and Ingram, L. O. (2008b) Eliminating side products and increasing succinate yields in engineered strains of *Escherichia coli* C, Biotechnol Bioeng 101, 881-893.

Jarboe, L. R., Zhang, X., Wang, X., Moore, J. C., Shanmugam, K. T., and Ingram, L. O. (2010) Metabolic engineering for production of biorenewable fuels and chemicals: contributions of synthetic biology, J Biomed Biotechnol 2010, 761042.

Kegel, A., Martinez, P., Carter, S. D., and Astrom, S. U. (2006) Genome wide distribution of illegitimate recombination events in *Kluyveromyces lactis*, Nucleic Acids Res 34, 1633-1645.

Kunioka, M., Ninomiya, F., and Funabashi, M. (2009) Biodegradation of poly(butylene succinate) powder in a controlled compost at 58 degrees C. evaluated by naturally-occurring carbon 14 amounts in evolved $CO(2)$ based on the ISO 14855-2 method, Int J Mol Sci 10, 4267-4283.

Lee, Y. J., Burlet, E., Galiano, F., Circu, M. L., Aw, T. Y., Williams, B. J., and Witt, S. N. (2011) Phosphate and succinate use different mechanisms to inhibit sugar-induced cell death in yeast: insight into the Crabtree effect, J Biol Chem 286, 20267-20274.

Lee, K. S., Kim, J. S., Heo, P., Yang, T. J., Sung, Y. J., Cheon, Y., Koo, H. M., Yu, B. J., Seo, J. H., Jin, Y. S., Park, J. C., and Kweon, D. H. (2012) Characterization of *Saccharomyces cerevisiae* promoters for heterologous gene expression in *Kluyveromyces marxianus*, Appl Microbiol Biotechnol.

Louie, T. M., Yang, H., Karnchanaphanurach, P., Xie, X. S., and Xun, L. (2002) FAD is a preferred substrate and an inhibitor of *Escherichia coli* general NAD(P)H:flavin oxidoreductase, J Biol Chem 277, 39450-39455.

Louie, T. M., Xie, X. S., and Xun, L. (2003) Coordinated production and utilization of FADH2 by NAD(P)H-flavin oxidoreductase and 4-hydroxyphenylacetate 3-monooxygenase, Biochemistry 42, 7509-7517.

Nair, N. U. and Zhao, H. M. (2009) Mutagenic inverted repeat assisted genome engineering (MIRAGE). Nucleic Acids Res 37, e9.

Neupert, W., and Herrmann, J. M. (2007) Translocation of proteins into mitochondria, Annu Rev Biochem 76, 723-749.

Neves, L., Oliveira, R. and Lucas, C. (2004) Yeast orthologues with glycerol transport and metabolism. FEMS Yeast Res 5, 51-62.

Niu, W., Draths, K. M., and Frost, J. W. (2002) Benzene-free synthesis of adipic acid, Biotechnol Prog 18, 201-211.

Nissen, T. L., Anderlund, M., Nielsen, J., Villadsen, J., and Kielland-Brandt, M. C. (2001) Expression of a cytoplasmic transhydrogenase in *Saccharomyces cerevisiae* results in formation of 2-oxoglutarate due to depletion of the NADPH pool, Yeast 18, 19-32.

Niviere, V., Fieschi, F., Decout, J. L., and Fontecave, M. (1999) The NAD(P)H:flavin oxidoreductase from *Escherichia coli*. Evidence for a new mode of binding for reduced pyridine nucleotides, J Biol Chem 274, 18252-18260.

Oura, E. (1977) Reaction products of yeast fermentations, Process Biochemistry 12, 19-21.

Palmieri, L., Vozza, A., Honlinger, A., Dietmeier, K., Palmisano, A., Zara, V., and Palmieri, F. (1999) The mitochondrial dicarboxylate carrier is essential for the growth of *Saccharomyces cerevisiae* on ethanol or acetate as the sole carbon source. Mol Microbiol 31. 569-577.

Palmieri, L., Lasorsa, F. M., Vozza, A., Agrimi, G., Fiermonte, G., Runswick, M. J., Walker, J. E., and Palmieri, F. (2000) Identification and functions of new transporters in yeast mitochondria, Biochim Biophys Acta 1459, 363-369.

Papagianni, M. (2007) Advances in citric acid fermentation by *Aspergillus niger*: biochemical aspects, membrane transport and modeling, Biotechnol Adv 25, 244-263.

Patel, M. A., Ou, M. S., Harbrucker, R., Aldrich, H. C., Buszko, M. L., Ingram, L. O., and Shanmugam, K. T. (2006) Isolation and characterization of acid-tolerant, thermophilic bacteria for effective fermentation of biomass-derived sugars to lactic acid, Appl Environ Microbiol 72, 3228-3235.

Raab, A. M. and Lang, C. (2011) Oxidative versus reductive succinic acid production in the yeast *Saccharomyces cerevisiae*. Bioengineered Bugs 2, 120-123.

Raab, A. M., Gebhardt, G., Bolotina, N., Weuster-Botz, D., and Lang, C. (2010) Metabolic engineering of *Saccharomyces cerevisiae* for the biotechnological production of succinic acid. Metabolic Engineering. 12: 518-525.

Raab, A. M., Hlavacek, V., Bolotina, N., and Lang, C. (2011) Shifting the fermentative/oxidative balance in *Saccharomyces cerevisiae* by transcriptional deregulation of the Snf1 upstream activating kinase Sak1p. Applied and Environmental Microbiology. 77: 1981-1989.

Roa Engel, C. A., Straathof, A. J., Zijlmans, T. W., van Gulik, W. M., and van der Wielen, L. A. (2008) Fumaric acid production by fermentation, Appl Microbiol Biotechnol 78, 379-389.

Robinson, K. M., and Lemire, B. D. (1996) Covalent attachment of FAD to the yeast succinate dehydrogenase flavoprotein requires import into mitochondria, presequence removal, and folding, J Biol Chem 271, 4055-4060.

Roper, D. I., Fawcett, T., and Cooper, R. A. (1993) The *Escherichia coli* C homoprotocatechuate degradative operon: hpc gene order, direction of transcription and control of expression, Mol Gen Genet 237, 241-250.

Rusche, L. N., and Rine, J. (2010) Switching the mechanism of mating type switching: a domesticated transposase supplants a domesticated homing endonuclease, Genes Dev 24, 10-14.

Saliola, M., Bartoccioni, P. C., De Maria, I., Lodi, T., and Falcone, C. (2004) The deletion of the succinate dehydrogenase gene KlSDH1 in *Kluyveromyces lactis* does not lead to respiratory deficiency, Eukaryot Cell 3, 589-597.

Saliola, M., Sponziello, M., D'Amici, S., Lodi, T., Falcone, C. (2008) Characterization of KlGUT2, a gene of the glycerol-3-phosphate shuttle, in *Kluyveromyces lactis*. FEMS Yeast Res 8, 697-705.

Sekar, B., Seol, E. and Park, S. (2017) Co-production of hydrogen and ethanol from glucose in *Escherichia coli* by activation of pentose phosphate pathway through deletion of phosphoglucose isomerase (pgi) and overexpression of glucose-6-phosphate dehydrogenase (zwf) and 6-phosphogluconate dehydrogenase (gnd). Biotechnology for Biofuels, 10:85-96.

Shao, Z., Luo, Y., and Zhao, H. (2012) DNA assembler method for construction of zeaxanthin-producing strains of *Saccharomyces cerevisiae*, Methods Mol Biol 898, 251-262.

Stein, I., Peleg, Y., Even-Ram, S., and Pines, O. (1994) The single translation product of the FUM1 gene (fumarase) is processed in mitochondria before being distributed between the cytosol and mitochondria in *Saccharomyces cerevisiae*, Mol Cell Biol 14, 4770-4778.

Sun, J., Shao, Z., Zhao, H., Nair, N., Wen, F., and Xu, J. H. (2012) Cloning and characterization of a panel of constitutive promoters for applications in pathway engineering in *Saccharomyces cerevisiae*, Biotechnol Bioeng 109, 2082-2092.

Tiwari, M. K., Singh, R. K., Lee, J. K., and Zhao, H. (2012) Mechanistic studies on the flavin:NADH reductase (PrnF) from *Pseudomonas fluorescens* involved in arylamine oxygenation, Bioorg Med Chem Lett 22, 1344-1347.

van Maris, A. J., Winkler, A. A., Porro, D., van Dijken, J. P., and Pronk, J. T. (2004) Homofermentative lactate production cannot sustain anaerobic growth of engineered *Saccharomyces cerevisiae*: possible consequence of energy-dependent lactate export, Appl Environ Microbiol 70, 2898-2905.

Vemuri, G. N., Eiteman, M. A., and altman, E. (2002) Effects of growth mode and pyruvate carboxylase on succinic acid production by metabolically engineered strains of *Escherichia coli*, App Enivron Microbiol 68, 1715-1727.

Vogtel, F. N., Wortelkamp, S., Zahedi, R. P., Becker, D., Leidhold, C., Gevaert, K., Kellermann, J., voos, W., Sickmann, A., Pfanner, N., and Meisinger, C. (2009) global analysis of the mitochondrial N-proteome idnetifies a processing peptidase critical for protein stability. Cell 139, 428-439.

Wach, A., Brachat, A., Pohlmann, R., and Philippsen, P. (1994) New heterologous modules for classical or PCR-based gene disruptions in *Saccharomyces cerevisiae*, Yeast 10, 1793-1808.

Wang, Q., Ingram, L. O., and Shanmugam, K. T. (2011) Evolution of D-lactate dehydrogenase activity from glycerol dehydrogenase and its utility for D-lactate production from lignocellulose, Proc Natl Acad Sci USA 108, 18920-18925.

Xu, G., Liu, L. and Chen, J. (2012) Reconstruction of cytosolic fumaric acid biosynthetic pathways in *Saccharomyces cerevisiae*. Microbial Cell Factories 11, 24-34.

Yuzbashev, T. V., Yuzbasheva, E. Y., Laptev, I. A., Sobolevskaya, T. I., Vybornaya, T. V., Larina, A. S., Gvilava, I. T., Antonova, S. V. and Sineoky, S. P. (2011) Is it possible to produce succinic acid at low pH? Bioengineered Bugs 2, 115-119.

Zelle, R. M., de Hulster, E., van Winden, W. A., de Waard, P., Dijkema, C., Winkler, A. A., Geertman, J. M., van Dijken, J. P., Pronk, J. T., and van Maris, A. J. (2008) Malic acid production by *Saccharomyces cerevisiae*: engineering of pyruvate carboxylation, oxaloacetate reduction, and malate export, Appl Environ Microbiol 74, 2766-2777.

Zhang, Q., Zhang, L., Ding, Z., and Shi, G. (2011) Metabolic engineering of wild acid-resistant yeast for L-lactic acid production. Chin. J. Biotech. 27, 1024-1031.

Zhang, X., Jantama, K., Moore, J. C., Jarboe, L. R., Shanmugam, K. T., and Ingram, L. O. (2009a) Metabolic evolution of energy-conserving pathways for succinate production in *Escherichia coli*, Proc Natl Acad Sci USA 106, 20180-20185.

Zhang, X., Jantama, K., Shanmugam, K. T., and Ingramb, L. O. (2009) Reengineering *Escherichia coli* for Succinate Production in Mineral Salts Medium, Appl Environ Microbiol 75, 7807-7813.

Zhang, Yiming, Zongjie Dai, Anastasia Krivoruchko, Yun Chen, Verena Siewers and Jens Nielsen (2015). Functional pyruvate formate lyase pathway expressed with two different electron donors in *Saccharomyces cerevisiae* at aerobic growth. FEMS Yeast Research, 15, 1-8

Zhu, L. W., Li, X. H. M., Liu, J. H., Yuan, Z. P., Chen, T., and Tang, Y. J. (2013) Activation of glyoxylate pathway without the activation of its related gene in succinate-producing engineered *Escherichia coli*, Meab. Eng 20C, 9-19.

What is claimed is:

1. A genetically modified yeast cell with increased succinic acid production, comprising at least one genetic modification that increases flux through the pentose phosphate pathway and a genetic modification that increases activity of enzymes for a cytoplasmic reductive pathway from phosphoenolpyruvate to succinate wherein said enzymes for a cytoplasmic reductive pathway comprising phosphoenolpyruvate carboxykinase (PCK), malate dehydrogenase (MDH), fumarase (FUM), and fumarate reductase (FRD).

2. The genetically modified yeast cell with increased succinic acid production of claim 1, wherein said at least one genetic modification that increases flux through the pentose phosphate pathway increases the activity of glucose-6-phosphate dehydrogenase (ZWF).

3. The genetically modified yeast cell with increased succinic acid production of claim 1, wherein said at least one genetic modification that increases flux through the pentose phosphate pathway decreases the activity of phosphoglucose isomerase (PGI).

4. The genetically modified yeast cell with increased succinic acid production of claim 1, wherein said at least one genetic modification that increases flux through the pentose phosphate pathway decreases the activity of phosphoglucose isomerase (PGI) and increases the activity of one or more enzymes chosen from the group consisting of glucose-6-phosphate dehydrogenase (ZWF), 6-phosphogluconate lactonase (PGL), and 6-phosphogluconate dehydrogenase (GND).

5. The genetically modified yeast cell with increased succinic acid production of claim 1, further comprising at least one genetic modification that increases the activity of malic enzyme (MAE).

6. The genetically modified yeast cell with increased succinic acid production of claim 5, further comprising at least one genetic modification that decreases the activity of a pyruvate carboxylase (PYC).

* * * * *